United States Patent
Yarnitzky

[11] Patent Number: 6,117,304
[45] Date of Patent: Sep. 12, 2000

[54] ELECTROANALYTICAL VOLTAMMETRIC CELL

[75] Inventor: Chaim Noah Yarnitzky, Haifa, Israel

[73] Assignee: VerdEco Technologies, Ltd., Yoqneam, Israel

[21] Appl. No.: 08/945,767

[22] PCT Filed: Apr. 30, 1996

[86] PCT No.: PCT/EP96/01795

§ 371 Date: Mar. 2, 1998

§ 102(e) Date: Mar. 2, 1998

[87] PCT Pub. No.: WO96/35118

PCT Pub. Date: Nov. 7, 1996

[30] Foreign Application Priority Data

May 1, 1995 [IL] Israel ......................................... 113563

[51] Int. Cl.$^7$ .............................. G01F 1/64; G01N 17/00; G01N 27/26
[52] U.S. Cl. ..................... 205/775; 205/789.5; 204/400; 204/412; 204/413; 204/273
[58] Field of Search .................................. 204/400, 412, 204/413, 273, 261; 205/775, 789, 789.5

[56] References Cited

U.S. PATENT DOCUMENTS

| | | | |
|---|---|---|---|
| 3,445,364 | 5/1969 | Strickler ................................... | 204/405 |
| 3,922,205 | 11/1975 | McLean et al. . | |
| 4,033,830 | 7/1977 | Fletcher, III ............................ | 204/400 |
| 4,066,406 | 1/1978 | Pungor et al. ........................... | 204/400 |
| 4,138,322 | 2/1979 | Barnes et al. . | |
| 4,186,607 | 2/1980 | Porter et al. ............................... | 73/422 |
| 4,233,031 | 11/1980 | Matson et al. ........................... | 204/400 |
| 4,260,467 | 4/1981 | Smith et al. . | |
| 4,786,373 | 11/1988 | Saloheimo et al. . | |
| 5,173,101 | 12/1992 | Novotny . | |
| 5,384,029 | 1/1995 | Campbell ................................. | 204/415 |
| 5,460,710 | 10/1995 | Williams et al. ....................... | 204/400 |

FOREIGN PATENT DOCUMENTS 2531224 2/1984 France .
WO 96/35117 11/1996 WIPO .

OTHER PUBLICATIONS

Analytical Chemistry, 59(15), 2014–2016 (1987) J. Wang, et al Modified Cell for Stripping . . . , Aug.

Primary Examiner—Robert J. Warden, Sr.
Assistant Examiner—Kaj K. Olsen
Attorney, Agent, or Firm—Eugene Lieberstein; Michael N. Meller

[57] ABSTRACT

An electroanalytical voltammetric cell containing:

(a) a cell body housing a counter electrode and a working electrode;
(b) means for causing a sample solution to flow through the cell and to fill a space between the counter-electrode and the working electrode; and
(c) a vibrator present in the space between the two electrodes which vibrates in order to fully mix the sample solution in the space.

6 Claims, 3 Drawing Sheets

ELECTROANALYTICAL VOLTAMMETRIC CELL

FIELD OF THE INVENTION

This invention relates to an improved voltammetric cell suitable for industrial use, and particularly for the analysis of sample solutions having extremely low concentration.

BACKGROUND OF THE INVENTION

Electrochemical detectors and voltammetric cells are known in the art and have been used with success for the analysis of flowing solution in the laboratory. Two-electrode and three-electrode cells are known. The three-electrode cell comprises a working electrode, a counter-electrode and a reference electrode which has the function of establishing and maintaining a constant potential relative to the working electrode or the sample solution. The sample solution is flown continuously through the cell. In principle, the electrodes may be affected by poisoning due to absorption with resulting passivation and loss of signal. In order to avoid such poisoning, the dropping mercury electrode has been adopted in many such cells.

U.S. Pat. No. 3,922,205 describes the basic structure of a voltammetric cell. U.S. Pat. No. 4,138,322 discloses a structure of shielded dropping mercury cathode. U.S. Pat. No. 4,260,467 describes a dropping mercury electrode which comprises a reservoir for liquid mercury, a mercury capillary at the outlet end of which mercury drops are formed, and a valve for selective air-purging passage of mercury from the reservoir to the inlet end of the capillary. An automated polarographic cell is described by C. N. Yarnitzky in Analytical Chemistry, Vol. 57, No. 9, August 1985, p. 2011–2015.

The efficiency of polarographic cells of the aforesaid type depends on the combination of a number of structural and functional features. A fully satisfactory combination, providing an industrially efficient such cell, has not been achieved so far in the art. The cells which are automatic and also on-line are expensive and not adequately efficient. In many cases, the prior art cells use a solid electrode which becomes polluted with time, so that the cell ceases to be reliable. In on-line, in-flow cells, the signal obtained is often proportional to the Reynolds number. Because of this, attempts have been made to design small cells, having high Reynolds number, comprising means for producing and controlling the dropping of the mercury electrode. Such means, however, being complicated and unreliable. Other cells are objectionable in that they require a very large volume of the sample solution, with resulting waste of time and chemicals.

A problem that is often encountered in the operation of voltammetric cells, both having drop mercury electrode and other electrodes, such as gold, platinum, glassy carbon etc., relates to their use for the analysis of sample solutions having an extremely low concentration. If the concentration falls to below 10 parts per billion, e.g., reaches the order of magnitude of tenths of parts per billion, a method known as stripping analysis must be used. This method involves passing an electric current through the static mercury drop electrode (SMDE) during one to three minutes so that the cationic material that is being analyzed accumulates in the static mercury drop, as would happen in normal electrolysis. Thereafter, the amount of material that has accumulated in the mercury drop is measured by measuring the current which passes between the mercury drop and the counter-electrode. Using this method requires extremely efficient mixing of the sample solution in the zone between the electrodes, which is difficult to achieve in small cells.

It is a purpose of this invention to provide an electroanalytical voltammetric cell, which is free from the drawbacks of the prior art cells.

It is another object of the invention to provide such a cell which is suitable for the analysis of sample solutions having an extremely low concentration.

It is a further object of the invention to provide such a cell in which a perfect mixing of the sample solution is obtained in the zone between the counter-electrode and the working electrode, particularly for the purpose of carrying out stripping analysis.

It is a still further purpose of the invention to provide all of the aforesaid features and advantages with a structure that is simple, reliable, inexpensive to make and durable in operation.

Other purposes and advantages of the invention will appear as the description proceeds.

SUMMARY OF THE INVENTION

The voltammetric cell, according to the invention, is characterized in that vibrator, particularly a magnetic vibrator, is provided in the space between the counter-electrode and the working electrode to vibrate as desired in order fully to mix the sample solution in the space between the aforesaid two electrodes. When the vibrator is a magnetic one, it is actuated by an external magnet.

In a form of the invention, the working electrode is a static mercury drop electrode (SMDE).

The cell according to the invention may, but need not, embody, besides the improvement provided by the invention, other improvements over the prior art as described in our copending application WO 96/35117, the contents of which are entirely incorporated herein by reference.

Correspondingly, the invention provides a method of voltammetric analysis, comprising the steps of providing a voltammetric cell having a working electrode, a counter-electrode located below said working electrode, and a reference electrode;

feeding the solution stream to a space between said working electrode and said counter-electrode; and exerting on the solution, in said space, a vibratory stirring action.

DETAILED DESCRIPTION OF PREFERRED EMBODIMENTS

Figure 1:
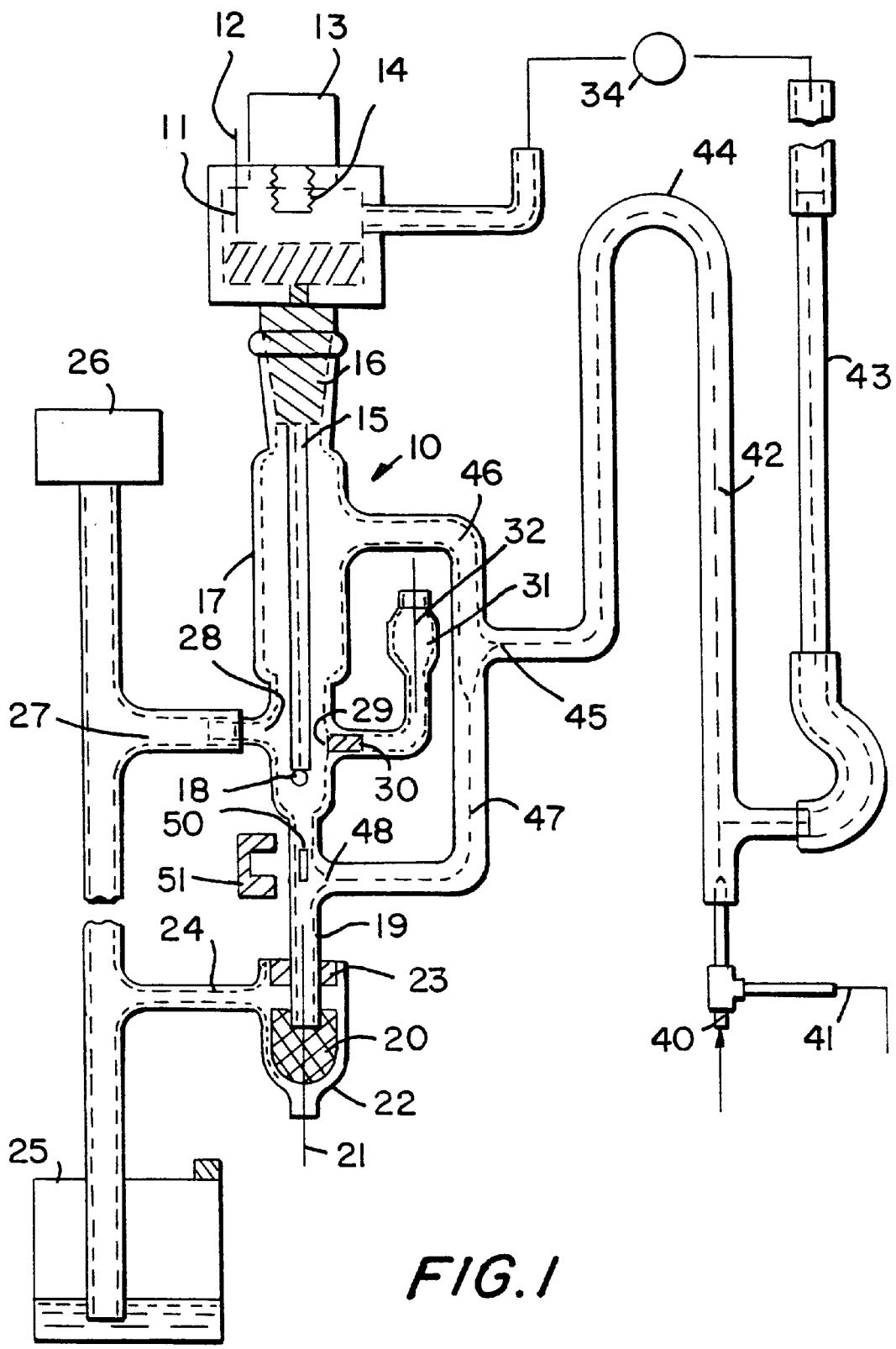
FIG. 1 is a schematic representation of a voltammetric cell, comprising an embodiment of the invention, seen in vertical cross-section.

The electroanalytical apparatus illustrated in FIG. 1 comprises a SMDE, but, as has been said, the working electrode could be of any other type, such as gold, platinum, glassy carbon, etc.

Said apparatus comprises a cell proper that is generally indicated at 10 and which comprises, staring at the top, a mercury reservoir 11. From reservoir 11, mercury flows to capillary 15 which passes through a stopper 16 of a suitable elastic matter, which closes the top of the cell body, generally indicated at 17, said cell body being preferably made of glass. A mercury drop 18 is formed at the end of capillary 15. Below the zone at which that drop is formed, the cell body 17 forms a pipe portion 19, which is full of sample solution. The sample solution is retained at the end of said pipe portion, because this latter sinks into a standing mercury mass 20. Said mercury mass, together with platinum wire 21, one end of which is immersed therein, constitutes the counter-electrode, and is contained in a reservoir 22, which is provided at its top with a stopper 23 through which pipe 19 passes. The reservoir 22 is connected with an outlet pipe 24. The mercury contained in the drops, which fall through pipe section 19 to reservoir 22, are added to mass 20. Concurrently, mercury overflows from reservoir 22 and is discharged through outlet 24 to sump 25.

A vacuum pump, not illustrated but schematically indicated at 26, applies suction to the cell through an exit pipe 27, which is connected to exit 28 formed in the body 17 of the cell. The cell body 17 is provided with another exit, 29, which is closed by a ceramic body 30 and leads to the reference electrode 31, such as a calomel electrode.

In this apparatus the sample solution is deoxygenated by means that will now be described. Said means embody improvements which are described and claimed in the aforementioned copending application WO 96/35117, but are not part of this invention, though it is desirable to apply them together with those of this invention. This invention could be applied to any other voltammetric cell, in which oxygen is not removed from the sample solution, or is removed by any suitable deoxygenation means, such as are known in the art or could be devised by skilled persons, without in any way departing from the present invention.

In the apparatus illustrated, therefore, a source of nitrogen, such as a pressure tank, not shown, is provided, as schematically indicated at 34. The sample solution, containing the electrolyte to be analyzed, is fed to the apparatus through inlets 40 and 41. It is drawn into the inlets by the vacuum applied to the cell, or by a peristaltic pump which feeds it to said inlets, or both. Through the said inlets, the solution is led into the stripping conduit, indicated in this embodiment as pipe 42, while nitrogen is fed to the same conduit through pipe 43. The pressure of the nitrogen prevents the solution from rising into pipe 43. Thus, the sample solution flows in a thin layer on the inner surface of pipe 42, while nitrogen flows centrally of said pipe; and oxygen is removed from the solution and becomes mixed with the nitrogen. Pipe 42 reaches its highest point, 44, and then continues downwardly to an outlet 45 where it branches out into an upper or gas branch 46 and a lower or liquid branch 47. At the outlet 45, the sample solution becomes separated from the nitrogen stream.

This latter flows upwardly through branch 46, while the sample solution flows downwardly through branch 47. The nitrogen flows into the body 17 of the cell, around mercury capillary 15, and out of it through exit 28 and pipe 27, to vacuum pump 26. The sample solution enters the cell body 17 at the inlet 48, situated between the mercury drop 18 and the pipe section 19. It is trapped in said pipe section by the mercury mass 20 and fills it completely, covering platinum electrode 21 and completely filing the space between the mercury mass 20 and the mercury drop 18. It then flows upwards over the mercury capillary 15 and finally out of the cell body 17 through outlet 28 and pipe 27, falling therefrom into sump 25. Means, not shown and conventional, are provided for applying a potential between the mercury contained in reservoir 11, and therefore the mercury drop 18, and the reference electrode 31–32.

Figure 2:
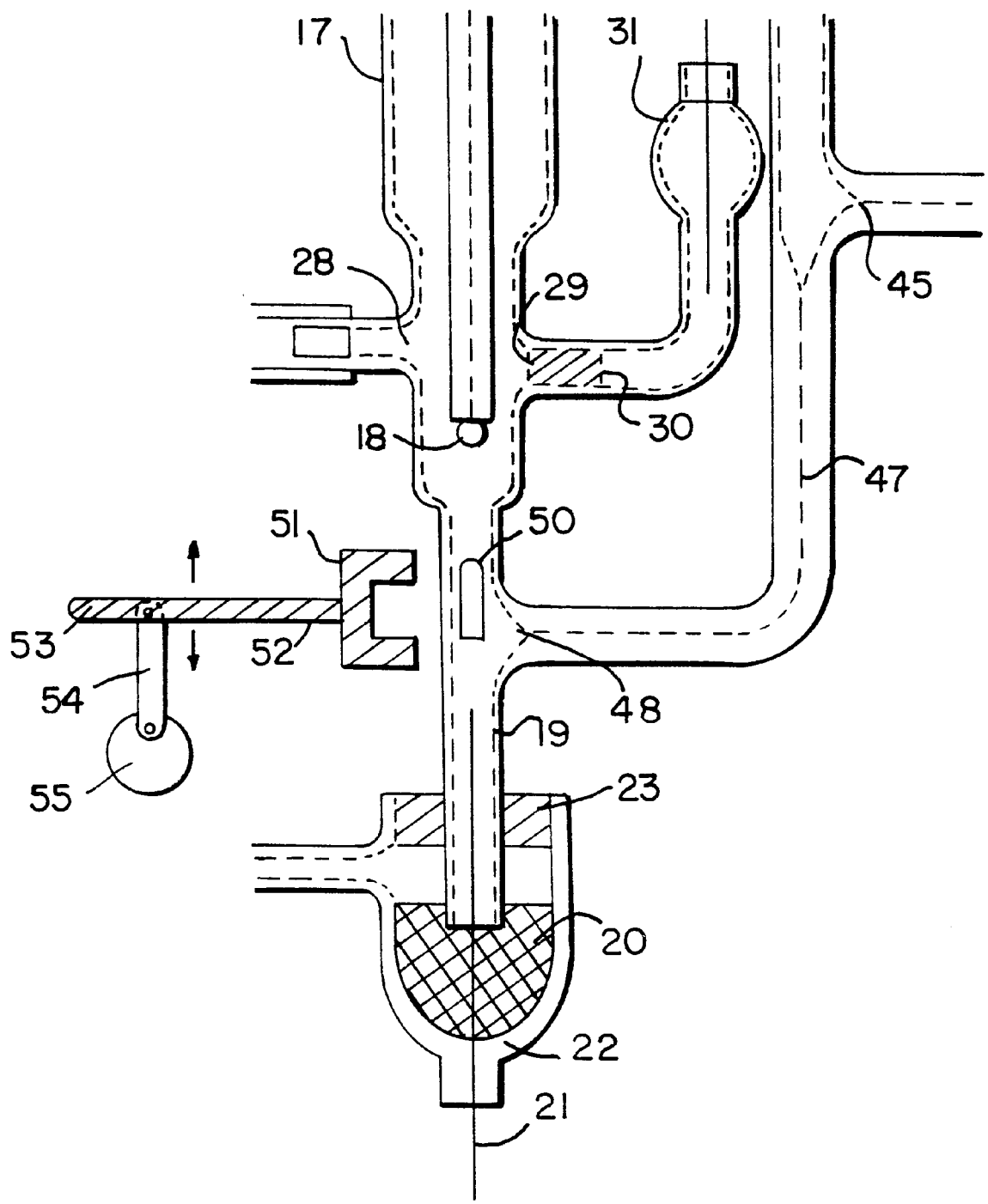
FIG. 2 is a detail, at an enlarged scale, of the part of the apparatus which comprises the elements that constitute an embodiment of the specific improvement of the invention.

According to the invention, between the working electrode, in this particular case the SMDE, and the counter-electrode, and approximately at the level of the inlet 48 into the cell body, a small magnet 50 is provided. This can be vibrated by means of an outer magnet 51 and will therefore mix the sample solution in the space between the working electrode and the counter electrode, whenever this is desired. These elements are better illustrated, at an enlarged scale, in FIG. 2. Numeral 52 indicates an oscillating lever on which magnet 51 is mounted. Lever 52 is pivoted at 53. A rotary element, schematically indicated as a disc 55, actuates lever 52, through a connecting rod 54, to oscillate about pivot 53, thereby causing magnet 51 to oscillate and draw magnet 50 into vibration within the solution contained in the cell body.

Figure 3:
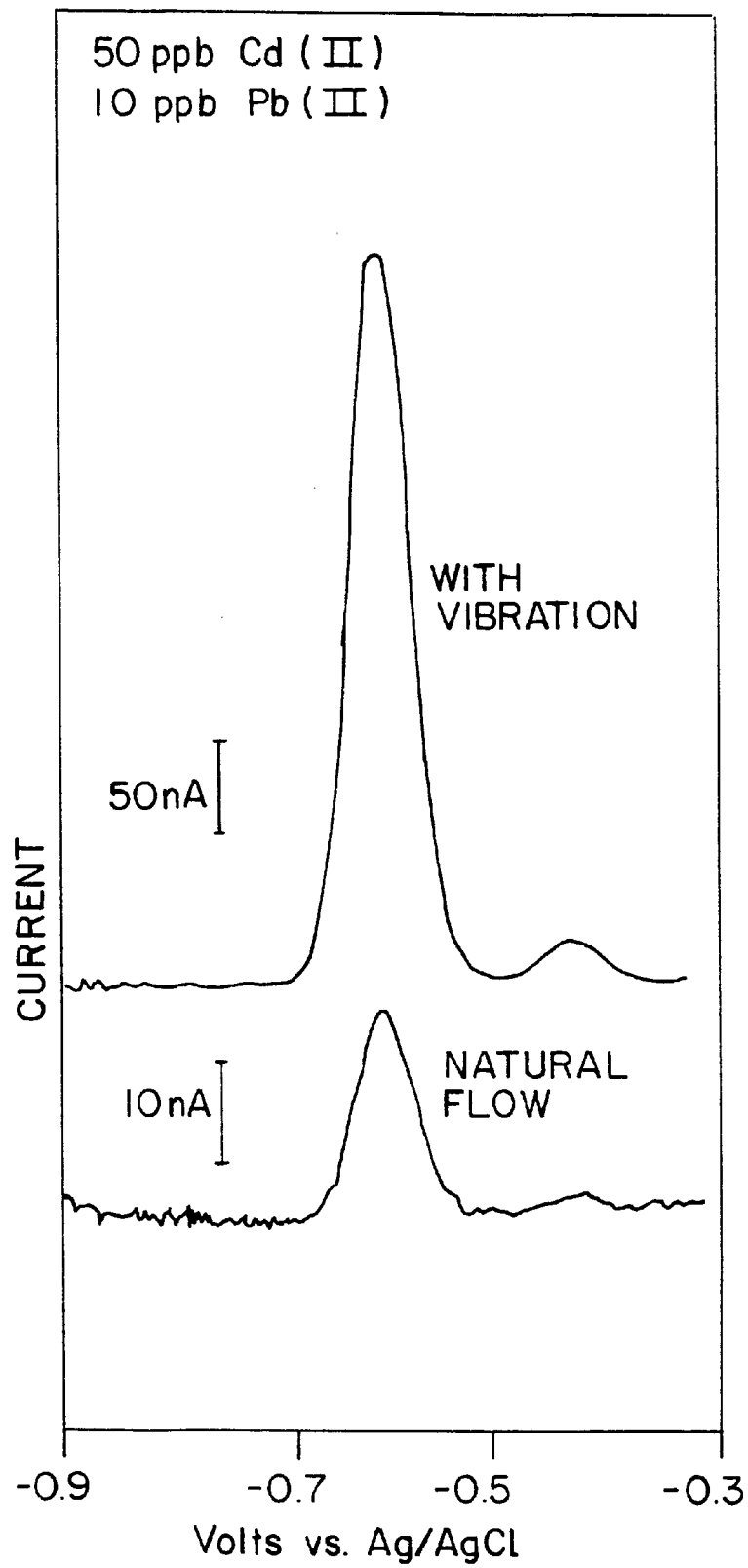
FIG. 3 is a diagram showing the increase in the peak of the current measured between the working electrode and the counter-electrode due to an application of the invention.

FIG. 3 illustrates the improvement produced by the application of the invention in the operation of voltammetric cell. It shows a diagram wherein the abscissa is the applied potential referred to Ag/AgCl, in volts, and the ordinate is the current measured between the working and the counter-electrodes, in nA. It is seen that when the solution is stirred by vibration, according to the invention, a current peak of 700 nA is measured, whereas if the vibration is stopped, the peak drops down to only 22 nA.

While an embodiment of the invention has been described by way of illustration, it will be apparent that the invention may be carried out by persons skilled in the art with many variations, modifications and adaptations, without departing from its spirit or exceeding the scope of the claims.

I claim:

1. An electroanalytical voltammetric cell which comprises:
   (a) a cell body housing a counter electrode and a working electrode, said counter electrode being located below the working electrode;
   (b) means for causing a sample solution to flow through the cell and to fill a space between the counter electrode and the working electrode; and
   (c) a vibrator provided in said space which vibrates in order to fully mix the sample solution in said space.

2. A cell according to claim 1, wherein the vibrator is a magnetic vibrator.

3. A cell according to claim 2, comprising an external magnet for actuating the vibrator.

4. A cell according to claim 1, wherein the working electrode is a static mercury drop electrode.

5. A method of voltammetric analysis comprising the steps of:
   (a) providing a voltammetric cell having a working electrode, a counter electrode located below the working electrode, a reference electrode and a vibrator positioned in a space between the working electrode and the counter electrode;
   (b) feeding a sample solution stream to said space; and
   (c) causing the vibrator to stir the solution in said space.

6. A method according to claim 5, wherein the vibrator is a magnetic rod actuated from outside the cell.

* * * * *